United States Patent [19]
Yokoo et al.

[11] Patent Number: 5,998,421
[45] Date of Patent: Dec. 7, 1999

[54] LIPID METABOLISM AMELIORANTS

[75] Inventors: Yoshiharu Yokoo, Hofu; Yoshinori Kobayashi, Tsukuba; Yumiko Nakano, Tsuchiura, all of Japan

[73] Assignee: Kyowa Hakko Kogyo Co., Ltd., Tokyo, Japan

[21] Appl. No.: 09/011,016

[22] PCT Filed: Jun. 12, 1997

[86] PCT No.: PCT/JP97/02034

§ 371 Date: Feb. 5, 1998

§ 102(e) Date: Feb. 5, 1998

[87] PCT Pub. No.: WO97/47209

PCT Pub. Date: Dec. 18, 1997

[30] Foreign Application Priority Data

Jun. 12, 1996 [JP] Japan ................... 8-150860

[51] Int. Cl.⁶ .................... A61K 31/505; A61K 31/40; A61K 31/405; A61K 35/78; A23K 1/00

[52] U.S. Cl. .................. 514/257; 514/408; 514/410; 514/411; 514/415; 424/195.1; 426/615

[58] Field of Search ................. 426/615; 424/195.1; 514/410, 411, 408, 257, 415, 909

[56] References Cited

U.S. PATENT DOCUMENTS

| | | | |
|---|---|---|---|
| 4,680,313 | 7/1987 | Iwai | 514/627 |
| 5,344,648 | 9/1994 | Haga et al. | 424/195.1 |
| 5,859,016 | 1/1999 | Suh et al. | 514/257 |

FOREIGN PATENT DOCUMENTS

| | | |
|---|---|---|
| 59-122414 | 7/1984 | Japan . |
| 60-224622 | 11/1985 | Japan . |
| 61-001619 | 1/1986 | Japan . |
| 62-148426 | 7/1987 | Japan . |
| 63-287724 | 11/1988 | Japan . |
| 3-264534 | 11/1991 | Japan . |
| 4-058303 | 9/1992 | Japan . |
| 4-305527 | 10/1992 | Japan . |
| 6-312932 | 11/1994 | Japan . |
| 6-343421 | 12/1994 | Japan . |

OTHER PUBLICATIONS

Nutr. Sci. Soy Protein, Japan, vol. 13 (1992) 53–58.
J. Pharm. Sci., vol. 75 No. 6 (1986) 612–613.
Eur. Journal of Pharmacology, vol. 215 (1992) 277–283.
Biol. Pharm. Bull., vol. 20, No. 3 (1997) 243–248.
Eur. Journal of Pharmacology, vol. 257 (1994) 59–66.
J. Cardiovascular Pharmacol., vol. 27, No. 6 (1996) 845–853.
Chem. Pharm. Bull., vol. 40, No. 9 (1992) 2325–2330.
J. Nat. Prod., vol. 42, No. 6 (1979) 697.
Planta medica, vol. 29 (1976) 310–317.

*Primary Examiner*—Kevin E. Weddington
*Attorney, Agent, or Firm*—Fitzpatrick, Cella, Harper & Scinto

[57] ABSTRACT

The present invention relates to a food and a feed having lipid metabolism improving activity or anti-obesity activity, and a lipid metabolism improving agent or an anti-obesity agent for humans or animals which comprise, as an active ingredient, a compound represented by formula (I):

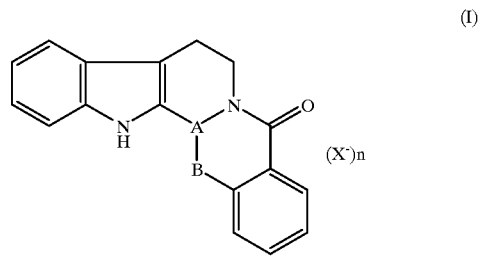

wherein >A—B— represents >CR¹—NR²— (wherein $R^1$ represents hydrogen or hydroxy, and $R^2$ represents hydrogen or lower alkyl; or $R^1$ and $R^2$ are combined together to form a bond) or >C=N⁺($R^3$)— (wherein $R^3$ represents lower alkyl); n represents 0 when >A—B— is >CR¹—NR²—, and represents 1 when >A—B— is >C=N⁺($R^3$)—; and X⁻ represents an anion, or a salt thereof.

11 Claims, No Drawings

LIPID METABOLISM AMELIORANTS

TECHNICAL FIELD

The present invention relates to a food, a drug and a feed which have lipid metabolism improving activity or anti-obesity activity.

BACKGROUND ART

The term lipid metabolism refers to the in vivo process of catabolism (decomposition) and anabolism (accumulation) of lipids, which are mainly triglycerides derived from food, and is intended to include, in the broad sense, reactions for transforming lipids into energy, biosynthesis of fatty acids, biosynthesis of acylglycerol, phospholipid metabolism, and cholesterol metabolism.

The term obesity means an excessive accumulation of fat in fat tissues of the parts of the body, and obesity is known to be closely related to hypertension, hyperlipidemia, diabetes, cerebral apoplexy, arteriosclerosis, myocardial infarction, etc.

Anti-obesity measures, or measures to treat or prevent obesity can be broadly classified into two groups; that is, control of energy intake and promotion of energy consumption. Examples of the former are intake of substitutes for sugar and fat, intake of dietary fibers contained in foods such as konjak (devil's-tongue jelly), and intake of absorption-inhibiting substances or appetite-depressing substances such as *Gymnema sylvestre* (Japanese Published Unexamined Patent Application No. 343421/94). Examples of the latter are exercise, and intake of lipid metabolism improving agents such as capsaicin (Japanese Published Examined Patent Application No. 58303/92) and soybean peptides {Daizu Tanpakushitsu Eiyo Kenkyukai Kaishi [Nutritional Science of Soy Protein (Japan)], 13, 53–58 (1992)}. However, it is difficult to continue exercise, and there is a limitation to capsaicin intake because of its hot taste. Thus, a need exists for a development of an effective lipid metabolism improving agent.

At present, rich feed is administered to livestock, poultry and cultivated fish with the aim of promoting their growth. As a result, a lipid metabolism abnormality sometimes occurs in these livestock, poultry and cultivated fish. As for pets, an excessive intake of feed and lack of exercise sometimes cause the problem of obesity.

Evodiamine is a compound obtained from *Evodia rutaecarpa* of the family Rutaceae, which is a kind of crude drug [Journal of Pharmaceutical Sciences, 75, 612–613 (1986)].

Evodiamine is known to have various pharmacological activities, for example, activities as a chilly constitution improving agent (Japanese Published Unexamined Patent Application No. 305527/92), a brain function improving agent (Japanese Published Unexamined Patent Application No. 287724/88), an anti-inflammatory agent for external use (Japanese Published Unexamined Patent Application No. 312932/94) and a cardiotonic (Japanese Published Unexamined Patent Application No. 224622/85), vasorelaxation activity [European Journal of Pharmacology, 215, 277–283 (1992)], and analgesic activity [Biol. Pharm. Bull., 20(3), 243–248 (1997)], as well as diuretic activity and sweating activity. However, there has been no report on lipid metabolism improving activity or anti-obesity activity thereof.

Rutaecarpine, dehydroevodiamine and hydroxyevodiamine are structurally analogous compounds which are obtained from *Evodia rutaecarpa* as well as evodiamine. The former two compounds have vasorelaxation activity like evodiamine [European Journal of Pharmacology, 257, 59–66 (1994), J. Cardiovasc. Pharmacol., 27(6), 845–853 (1996)]. Further, rutaecarpine has analgesic activity as well as evodiamine [Biol. Pharm. Bull., 20(3), 243–248 (1997)]. However, there has been no report on the above three compounds in respect of lipid metabolism improving activity or anti-obesity activity.

*Evodia rutaecarpa*, which is a plant belonging to the genus Evodia, is not only used as a stomachic, a diuretic and an analgesic, but also is known to have activities as a hair-nourishing food (Japanese Published Unexamined Patent Application No. 1619/86), cosmetics containing extract of *Evodia rutaecarpa* (Japanese Published Unexamined Patent Application No. 122414/84), an alcohol absorption-inhibiting agent (Japanese Published Unexamined Patent Application No. 264534/91), and a therapeutic agent for periodontal disease (Japanese Published Unexamined Patent Application No. 148426/87). However, there has been no report on lipid metabolism improving activity or anti-obesity activity thereof.

*Fagara rhetza*, which is an Indonesian traditional medicinal herb belonging to the genus Fagara, is known to have an effect on malaria, diarrhea and vomiting [Chem. Pharm. Bull., 40(9), 2325–2330 (1992)]. However, no report has been made on lipid metabolism improving activity or anti-obesity activity thereof.

*Zanthoxylum rhetsa* and *Zanthoxylum budrunga*, which are plants belonging to the genus Zanthoxylum, have been reported to have cytotoxicity [J. Nat. Prod., 42(6), 697 (1979)]. However, no report has been made on lipid metabolism improving activity or anti-obesity activity thereof.

*Araliopsis tabouensis* and *Araliopsis soyauxii*, which are plants belonging to the genus Araliopsis, are known to have an effect on gonorrhea [Planta medica, 29, 310–317 (1976)]. However, no report has been made on lipid metabolism improving activity or anti-obesity activity thereof.

DISCLOSURE OF THE INVENTION

The present invention relates to a food having lipid metabolism improving activity or anti-obesity activity which comprises, as an active ingredient, a compound selected from the group consisting of compounds represented by formula (I):

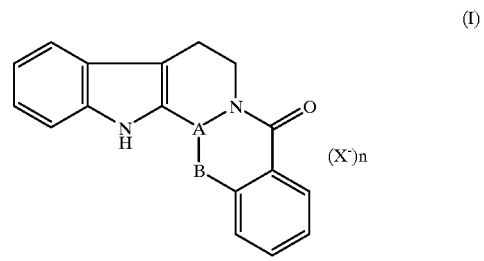

wherein >A—B— represents >CR$^1$—NR$^2$— (wherein R$^1$ represents hydrogen or hydroxy, and R$^2$ represents hydrogen or lower alkyl; or R$^1$ and R$^2$ are combined together to form a bond) or >C=N$^+$(R$^3$)— (wherein R$^3$ represents lower alkyl); n represents 0 when >A—B— is >CR$^1$—NR$^2$—, and represents 1 when >A—B— is >C=N$^+$(R$^3$)—; and X$^-$ represents an anion, and salts thereof (hereinafter collectively referred to as evodiamine compounds).

The present invention also relates to a lipid metabolism improving agent or an anti-obesity agent which comprises an evodiamine compound as an active ingredient; a method for lipid metabolism improvement or anti-obesity which comprises administering an effective amount of an evodiamine compound; the use of an evodiamine compound for the preparation of a pharmaceutical composition which is useful for lipid metabolism improvement or anti-obesity; the use of an evodiamine compound for lipid metabolism improvement or anti-obesity; and a composition for lipid metabolism improvement or anti-obesity which comprises, in pharmaceutically acceptable dosage form, an effective amount of an evodiamine compound in association with a pharmaceutically acceptable carrier.

Further, the present invention relates to a feed having lipid metabolism improving activity or anti-obesity activity which comprises an evodiamine compound as an active ingredient.

Furthermore, the present invention relates to a feed additive having lipid metabolism improving activity or anti-obesity activity which comprises an evodiamine compound as an active ingredient; a method for lipid metabolism improvement or anti-obesity of an animal which comprises administering an effective amount of an evodiamine compound; the use of an evodiamine compound for the preparation of a feed additive which is useful for lipid metabolism improvement or anti-obesity; the use of an evodiamine compound for lipid metabolism improvement or anti-obesity of an animal; and a composition for lipid metabolism improvement or anti-obesity of an animal which comprises, in pharmaceutically acceptable dosage form, an effective amount of an evodiamine compound in association with a pharmaceutically acceptable carrier.

In the definitions of the groups in formula (I), the lower alkyl represented by $R^2$ and $R^3$ means a straight-chain or branched alkyl group having 1–6 carbon atoms, such as methyl, ethyl, propyl, isopropyl, butyl, sec-butyl, tert-butyl, pentyl, neopentyl and hexyl. Preferred is methyl.

Examples of the anions are hydrogen ion, halogen ions, anions derived from inorganic acids and anions derived from organic acids. Examples of the halogen ions are fluorine ion, chlorine ion, bromine ion and iodine ion. Examples of the anions derived from inorganic acids are nitrate ion, sulfate ion, phosphate ion and carbonate ion. Examples of the anions derived from organic acids are formate ion, acetate ion, lactate ion, citrate ion, and anions derived from carboxylic acids such as glutamic acid.

Examples of the salts are acid addition salts, e.g. hydrochloride, and organic acid addition salts such as maleate, tartrate and citrate.

The evodiamine compounds represented by formula (I) include evodiamine, rutaecarpine, dehydroevodiamine, hydroxyevodiamine, etc.

Evodiamine is a compound represented by formula (II):

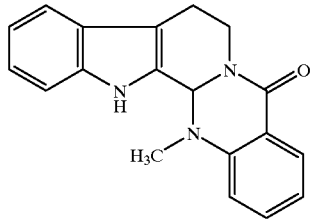

(II)

Evodiamine is commercially available (a product of Kishida Chemical Co., Ltd.). It can also be prepared according to the chemical synthesis methods described in Japanese Published Unexamined Patent Application No. 77098/77, Japanese Published Examined Patent Application No. 434/83 [(R,S)-evodiamine], J. Chem. Soc. Chem. Commun. 10, 1092–1093 (1982) [(S)-evodiamine], etc., or can be obtained from evodiamine-containing plants, for example, plants belonging to the family Rutaceae such as plants of the genus Evodia (*Evodia rutaecarpa, E. officinalis, E. danielli, E. meliaefolia*, etc.), the genus Fagara (*Fagara rhetza*, etc.), the genus Zanthoxylum (*Zanthoxylum rhetsa, Z. budrunga, Z. flavum*, etc.), and the genus Araliopsis (*Aralioisis tabouensis, A. soyauxii*, etc.) according to, for example, the method described in Journal of Pharmaceutical Sciences, 75, 612–613 (1986).

Evodiamine has optical isomers: both the S-form and the R-form are obtained according to the chemical synthesis methods, and the S-form is obtained from the plants. In the present invention, any of the S-form, the R-form, and the mixture thereof may be used. Preferred is the S-form.

Rutaecarpine is a compound represented by formula (III):

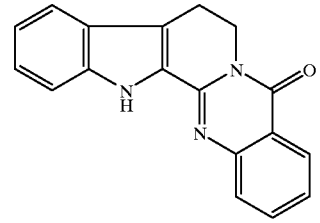

(III)

Rutaecarpine is commercially available (a product of Kishida Chemical Co., Ltd.). It can also be prepared according to the chemical synthesis methods described in Japanese Published Unexamined Patent Application No. 77100/78, J. Org. Chem., 50, 1246–1255 (1985), etc., or can be obtained from rutaecarpine-containing plants, for example, plants belonging to the family Rutaceae such as plants of the genus Evodia (*Evodia rutaecarpa, E. meliaefolia*, etc.), the genus Fagara (*Fagara rhetza*, etc.), and the genus Zanthoxylum (*Zanthoxylum rhetsa, Z. limonella, Z. integrifoliolum*, etc.) according to, for example, the method described in Chem. Pharm. Bull., 37, 1820–1822 (1989).

Dehydroevodiamine is a compound represented by formula (IV):

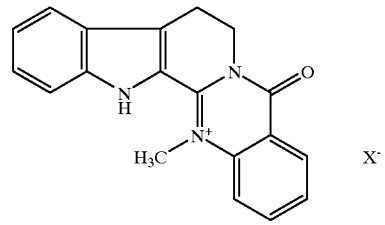

(IV)

wherein $X^-$ represents an anion, which has the same significance as described above. Dehydroevodiamine can be prepared according to the chemical synthesis method described in J. Org. Chem., 50, 1246–1255 (1985), etc., or can be obtained from dehydroevodiamie-containing plants, for example, plants belonging to the family Rutaceae such as plants of the genus Evodia (*Evodia rutaecarpa, E. meliaefolia*, etc.) according to, for example, the method described in American Journal of Chinese Medicine, 10, 75–85 (1982).

Hydroxyevodiamine is a compound represented by formula (V):

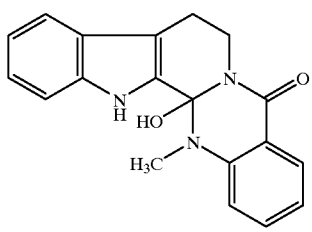

(V)

Hydroxyevodiamine can be obtained from hydroxyevodiamine-containing plants, for example, plants belonging to the family Rutaceae such as plants of the genus Evodia (*Evodia rutaecarna*, etc.), the genus Zanthoxylum (*Zanthoxylum rhetsa*, etc.), and the genus Araliopsis (*Araliopsis tabouensis*, etc.) according to, for example, the method described in J. of the Pharmaceutical Society of Japan, 82, 619–626 (1962).

As the evodiamine compounds in the present invention, purified products or pure preparations can be used, but crude ones or partially-purified ones may also be used as long as they do not contain impurities which are inappropriate as components of foods, drugs or feeds.

Examples of the crude or partially-purified evodiamine compounds are parts (e.g. leaves, trunks, bark, roots and fruits) of plants which contain evodiamine compounds, preferably plants belonging to the family Rutaceae, more preferably plants belonging to the genus Evodia, Fagara, Zanthoxylum or Araliopsis, and ground matters, extracts, crude products and purified products containing evodiamine compounds which are obtained from said parts of the plants.

As the parts of the plants containing evodiamine compounds, fruits, bark and root bark of the plants such as *Evodia rutaecarpa, Fagara rhetza, Zanthoxylum rhetsa, Araliopsis tabouensis* and *Evodia meliaefolia* are preferably used.

The ground matters containing evodiamine compounds can be obtained by drying and then grinding the parts of the plants containing evodiamine compounds.

The extracts containing evodiamine compounds can be obtained by extraction from said ground matters using water, hydrophilic solvents, e.g. alcohols such as methanol, ethanol, propanol and butanol, and acetone, and organic solvents such as diethyl ether, ethyl acetate, chloroform and benzene, alone or in combination.

The partially-purified or purified products of evodiamine compounds can be obtained by subjecting said ground matters or extracts to fractional purification by means of column chromatography or preparative high performance liquid chromatography using a porous polymer such as DIAION HP-20 (registered trademark, Mitsubishi Chemical Co., Ltd.), Sephadex such as Sephadex LH-20 (registered trademark, Pharmacia LKB Biotechnology Co., Ltd.), normal phase silica gel, reversed-phase silica gel, polyamide, activated carbon or cellulose. In this purification step, detection of the desired component is carried out by thin layer chromatography (developing solvent: 95% methanol, color developing agent: 5% ethanol sulfate). It is desirable to appropriately combine or repeat the above treatments, and if necessary, to carry out recrystallization in order to prepare the purified products or the pure preparations of evodiamine compounds.

The food of the present invention can be prepared by adding an evodiamine compound to food materials, particularly, those containing substantially no evodiamine compound by nature in a conventional process for producing a food. The evodiamine compound is added in the form of a pure preparation, a purified product, a partially-purified product, a lipid metabolism improving agent or an anti-obesity agent, in such an amount that the content of the compound in the food becomes 0.001% or more, preferably 0.01–20%, more preferably 0.05–1%.

Examples of the foods are juice, soft drinks, tea, lactic acid beverages, fermented milk, ices, dairy products (e.g. butter, cheese, yogurt, processed milk and skim milk), meat products (e.g. ham, sausage and hamburger), fish products (e.g. steamed, baked or fried fish paste), egg products (e.g. fried or steamed foods made of beaten eggs), confectionery (e.g. cookies, jelly and snacks), bread, noodles, pickles, smoked fish and meat, dried fish, preserved foods boiled down with soy, salted foods, soup and seasonings.

The food of the present invention may be in any of the forms such as a frozen food, a powder food, a sheet-shaped food, a bottled food, a canned food, a retort food, a capsule food and a tablet food, and may also be in the form of a liquid food, a pre-digested nutrient food, an elemental diet, a liquid nutrient food, or the like formulated to contain a protein, a sugar, a fat, a trace element, a vitamin, an emulsifier, a flavor, etc., as long as the food contains an evodiamine compound.

The food of the present invention can be used as a health food or a functional food not only for slimming diet but also for the treatment, prevention or alleviation of diseases such as fatty liver, hypertension, hyperlipidemia, arteriosclerosis, diabetes and myocardial infarction. It is preferred that an evodiamine compound is ingested in an amount of 0.1–2000 mg/day from the processed food of the present invention.

The lipid metabolism improving agent or the anti-obesity agent of the present invention may be in any of the dose forms such as tablets, powders, fine granules, granules, capsules, syrups, enteric coated tablets, troches, injections and infusions. The administration route for said agent is not specifically limited. Examples of suitable administration routes are oral administration, intravenous administration, intraperitoneal administration, subcutaneous administration and intramuscular administration. Preferred is oral administration. In the case of oral administration, a pure preparation, a purified product or a partially-purified product of an evodiamine compound can be administered as it is, or in the form of compositions such as tablets, powders, fine granules, granules, capsules and syrup containing pharmaceutically acceptable excipients. As the excipients, saccharides such as sorbitol, lactose, glucose, dextrin, starch and crystalline cellulose, inorganic substances such as calcium carbonate and calcium sulfate, distilled water, sesame oil, corn oil, olive oil, cottonseed oil, and other generally employed excipients can be used. In preparing the compositions, additives such as binders, lubricants, dispersing agents, suspending agents, emulsifiers, diluents, buffers, antioxidants and antibacterial agents may be used. Injectable preparations can be prepared by adding an appropriate buffer, an isotonicity agent, etc. to an active compound and dissolving the mixture in an oil such as a vegetable oil.

The dose of said agent will vary depending on various factors such as the patient's age, sex and physical condition, administration route, administration schedule, and form of the agent. For instance, when the agent is orally administered to an adult, it is suitable to administer an evodiamine compound as an active ingredient in an amount of 0.1–2000 mg/day in 1 to 4 parts. Administration may be made at a dose outside the above limit as may be required.

The lipid metabolism improving agent or the anti-obesity agent of the present invention can be used for the treatment or prevention of diseases such as fatty liver, hypertension, hyperlipidemia, arteriosclerosis, diabetes and myocardial infarction, and obesity.

The feed of the present invention includes any feed comprising an evodiamine compound which has lipid metabolism improving activity or anti-obesity activity on animals such as mammals, birds, reptiles, amphibians and fish. Suitable examples are feed for pets such as dogs, cats and mice, feed for livestock such as cows and pigs, feed for poultry such as hens and turkeys, and feed for cultivated fish such as sea breams and young yellowtails.

As the feed additive of the present invention, any of the following substances can be used: an evodiamine compound in the form of a pure preparation, a purified product or a partially-purified product; parts of plants containing an evodiamine compound; and a ground matter, extract, a partially-purified product or a purified product containing an evodiamine compound which is obtained from said plant parts. If necessary, the feed additives may be made into the form of powder, fine granules, pellets, tablets, various liquids, etc. by mixing or dissolution in a conventional manner.

The feed of the present invention can be prepared by adding the above feed additive to a feed. The amount of the feed additive of the present invention to be added to the feed is appropriately selected depending on the kind of feed, the effect expected by intake of the feed, etc. Generally, the feed of the present invention can be prepared by adding the feed additive of the present invention to feed materials, particularly, those containing substantially no evodiamine compound by nature in a conventional process for producing a feed, in such an amount that the content of an evodiamine compound in the feed becomes 0.001% or more, preferably 0.01–20%, more preferably 0.05–1%.

TEST EXAMPLE 1
Effect on Visceral Fat of a Mouse

The following experiment was carried out using a feed containing evodiamine.

Nine-weeks-old male C3H mice were preliminarily fed with Feed A containing no evodiamine which was prepared according to the composition of Table 1 for 8 days, and then divided into 2 groups each consisting of 4 animals. One of the groups (Feed A group) was fed with Feed A and the other group (Feed B group) was fed with Feed B containing evodiamine which was prepared according to the composition of Table 1 for 12 days. After being fasted for one day, the mice of both groups were killed on the 13th day. The perirenal adipose tissue and the epididymal adipose tissue of each mouse were excised immediately and weighed. The feed intake was measured every day during the test period.

TABLE 1

| | Feed A<br>% (w/w) | Feed B<br>% (w/w) |
|---|---|---|
| Evodiamine | — | 0.03 |
| Casein | 20 | 20 |
| Lard | 10 | 10 |
| Sucrose | 10 | 10 |
| Mineral mixture | 4 | 4 |
| Vitamin mixture | 1 | 1 |
| Cellulose powder | 2 | 2 |
| Sodium cholate | 0.125 | 0.125 |
| Choline chloride | 0.2 | 0.2 |
| Corn starch | 52.675 | 52.645 |

The results are shown in Table 2.

TABLE 2

| | Feed A group | Feed B group |
|---|---|---|
| Average feed intake (g/day) | 3.30 ± 0.08* | 3.21 ± 0.09 |
| Epididymal adipose tissue (g) | 0.246 ± 0.019 | 0.219 ± 0.010 |
| Perirenal adipose tissue (g) | 0.116 ± 0.01[a] | 0.083 ± 0.08 |

*Standard error of the average value
[a]The difference between the two groups was significant ($P < 0.05$)

The amount of the perirenal adipose tissue in Feed B group was significantly smaller than that in Feed A group. The amount of the epididymal adipose tissue was also somewhat smaller in Feed B group. There was no significant difference in feed intake between the two groups, which suggests that there is no taste problem. Thus, it was confirmed that evodiamine had lipid metabolism improving activity or anti-obesity activity.

TEST EXAMPLE 2
Effect on Weight, Visceral Fat and Lipolysis of a Rat

The following experiment was carried out using a feed containing extract of *Evodia rutaecarpa* prepared in Reference Example 1.

Four-weeks-old male SD rats were preliminarily fed with low-fat Feed C containing no extract of *Evodia rutaecarpa* which was prepared according to the composition of Table 3 for 7 days. The rats were then divided into 9 groups each consisting of 3 animals in such a way that there is no significant difference in body weight of the animals among the groups. One rat in each group was fed with Feed E which is a high-fat feed containing the extract of *Evodia rutaecarpa* after one-day fast. The other two rats in each group were given, by pair-feeding, Feed C which is a low-fat feed without the extract of *Evodia rutaecarpa* and Feed D which is a high-fat feed without the extract of *Evodia rutaecarpa*, respectively, in an amount equal to the feed intake of the rat fed with Feed E in the same group. As Feed C and Feed E have different fat contents, when they are taken in the same amounts, the calorie intake from Feed C is about 78% of that from Feed E. After the breeding by the above pair-feeding was continued for 21 days, the rats were fasted for one day and then killed. The perirenal adipose tissue and the epididymal adipose tissue of each rat were excised immediately and weighed. The lipolytic activity was also determined in the following manner. The body weight was measured every day during the test period.

Determination of the Lipolytic Activity:

After the perirenal adipose tissue of each rat was cut into pieces with scissors 50 times, 100–300 mg of the cut tissue was weighed, and 1.9 ml of Krebs-Ringer bicarbonate buffer (hereinafter abbreviated as KRB buffer) containing 2% albumin was added thereto to prepare two samples. These samples were subjected to reaction at 37° C. for 5 minutes. To one of the samples was added 0.1 ml of KRB buffer containing 0.2 mg/ml noradrenaline-2% albumin, and the mixture was subjected to reaction at 37° C. for one hour to make a reaction sample. To the other sample was added 0.1 ml of KRB buffer containing 2% albumin, and the mixture was ice-cooled for 5 minutes to make a pre-reaction control sample. Each sample was filtered using a membrane filter (0.45 μm, Millipore Corp.) and the amount of free fatty acids in the filtrate was determined using a commercially available determination kit (Determiner NEFA, Kyowa Medex Co., Ltd.). Then, the amount of triglycerides decomposed was calculated. The activity value was obtained by subtracting the value of the pre-reaction control sample from the value of the reaction sample.

TABLE 3

|  | Feed C % (w/w) | Feed D % (w/w) | Feed E % (w/w) |
| --- | --- | --- | --- |
| Extract of *Evodia rutaecaroa* (Reference Example 1) | — | — | 1.35 |
| Casein | 20 | 20 | 20 |
| Lard | 5 | 15 | 15 |
| Corn oil | 5 | 15 | 15 |
| Sucrose | 30 | 30 | 30 |
| Mineral mixture | 4 | 4 | 4 |
| Vitamin mixture | 1 | 1 | 1 |
| Cellulose powder | 2 | 2 | 2 |
| Choline Chloride | 0.2 | 0.2 | 0.2 |
| Corn starch | 32.80 | 12.80 | 11.45 |
| Evodiamine concentration (w/w %) | 0 | 0 | 0.02 |

The results are shown in Table 4.

TABLE 4

|  | Feed C group | Feed D group | Feed E group |
| --- | --- | --- | --- |
| Calorie intake (cal/21 days) | $1101.8 \pm 16.0^{*c}$ | $1421.6 \pm 21.7$ | $1410.9 \pm 21.4$ |
| Last body weight (g) | $215.2 \pm 3.6$ | $252.7 \pm 3.5^c$ | $226.8 \pm 4.3$ |
| Body weight increase (g) | $101.3 \pm 2.6^a$ | $138.2 \pm 2.9^c$ | $112.3 \pm 3.8$ |
| Body weight increase/calorie intake (g/cal) | $0.0920 \pm 0.0020^b$ | $0.0972 \pm 0.0011^c$ | $0.0797 \pm 0.0029$ |
| Epididymal adipose tissue (g) | $3.19 \pm 0.25^b$ | $4.06 \pm 0.24^c$ | $2.28 \pm 0.14$ |
| Perirenal adipose tissue (g) | $3.70 \pm 0.30$ | $5.68 \pm 0.39^c$ | $3.06 \pm 0.27$ |
| Lipolytic activity ($\mu$mol/g/hr) | $2.75 \pm 0.81^b$ | $3.19 \pm 0.34^b$ | $6.35 \pm 0.93$ |

*Standard error of the average value
[a,b,c]The difference between Feed C or D group and Feed E group was significant (a: $P < 0.05$, b: $P < 0.01$, c: $P < 0.001$).

The body weight increase was significantly reduced in Feed E group compared with that in Feed D group which had almost the same calorie intake. Feed E group showed significantly less body weight increase per calorie intake as compared not only with Feed D group but also with Feed C group which had a smaller total calorie intake.

The amounts of the perirenal adipose tissue and the epididymal adipose tissue in Feed E group were significantly smaller than those in Feed D group. Further, as compared with the results on Feed C group which had a smaller total calorie intake, the amount of the epididymal adipose tissue in Feed E group was significantly smaller, and that of the perirenal adipose tissue was also somewhat smaller.

Feed E group showed significantly higher lipolytic activity as compared with Feed C group and Feed D group, which indicates that lipid metabolism was improved in Feed E group. Thus, it was confirmed that the extract of *Evodia rutaecarpa* containing evodiamine had lipid metabolism improving activity or anti-obesity activity.

BEST MODE FOR CARRYING OUT THE INVENTION

EXAMPLE 1

Cookies (30 pieces) are prepared from the following ingredients.

| Soft flour | 100 g |
| --- | --- |
| Starch | 74 g |
| Water | 14 g |
| Evodiamine | 0.6 g |
| Baking powder | 2 Tsp. |
| Salt | ½ Tsp. |
| Egg | one |
| Butter | 80 g |
| Milk | 2 Tbsp. |
| Honey | Small quantity |

EXAMPLE 2

A soft drink (10 bottles) is prepared from the following ingredients.

| Evodiamine | 1 g |
| --- | --- |
| Vitamin C | 1 g |
| Vitamin B1 | 5 mg |
| Vitamin B2 | 10 mg |
| Vitamin B6 | 25 mg |
| Sugar syrup | 150 g |
| Citric acid | 3 g |
| Flavor | 1 g |

Water is added to make a volume of 1000 ml.

EXAMPLE 3

Bread (4 loaves) is prepared from the following ingredients.

| Evodiamine | 2.4 g |
| --- | --- |
| Hard flour | 1 kg |
| Sugar | 50 g |
| Salt | 20 g |
| Skim milk | 20 g |
| Shortening | 60 g |
| Yeast (fresh) | 30 g |
| Yeast food | 1 g |
| Water | 650 g |

EXAMPLE 4

Tablets (300 mg/tablet) are prepared from the following ingredients according to a conventional method.

| Evodiamine | 10 mg |
| --- | --- |
| Lactose | 230 mg |
| Corn starch | 30 mg |
| Synthetic aluminum silicate | 12 mg |
| Carboxymethyl cellulose calcium | 15 mg |
| Magnesium stearate | 3 mg |

EXAMPLE 5

A powder preparation (1000 mg/package) is prepared from the following ingredients according to a conventional method.

| Evodiamine | 10 mg |
| --- | --- |
| Lactose | 800 mg |
| Corn starch | 190 mg |

EXAMPLE 6

Hard capsules (360 mg/capsule) are prepared from the following ingredients.

| Evodiamine | 10 mg |
| --- | --- |
| Lactose | 230 mg |
| Corn starch | 100 mg |
| Hydroxypropyl cellulose | 20 mg |

Evodiamine (10 mg) is mixed with 230 mg of lactose and 100 mg of corn starch, and 20 mg of an aqueous solution of hydroxypropyl cellulose is added thereto. The mixture is kneaded and then granulated according to a conventional method using an extruding granulator. The obtained granules are packed in gelatin hard capsules.

EXAMPLE 7

Soft capsules (170 mg/capsule) are prepared from the following ingredients.

| Evodiamine | 10 mg |
| --- | --- |
| Soybean oil | 160 mg |

Evodiamine (10 mg) is mixed with 160 mg of soybean oil. The resulting mixture is packed in soft capsules according to a conventional method using a rotary dies automatic molding machine.

EXAMPLE 8

A feed for a mouse (ration for one month) is prepared from the following ingredients.

| Evodiamine | 0.03 g |
| --- | --- |
| Casein | 20 g |
| Lard | 10 g |
| Sucrose | 10 g |
| Mineral mixture | 4 g |
| Vitamin mixture | 1 g |
| Cellulose powder | 2 g |
| Sodium cholate | 0.125 g |
| Choline chloride | 0.2 g |
| Corn starch | 52.645 g |

EXAMPLE 9

A powder preparation (1000 mg/package) is prepared from the following ingredients according to a conventional method.

| Rutaecarpine | 10 mg |
| --- | --- |
| Lactose | 800 mg |
| Corn starch | 190 mg |

EXAMPLE 10

Soft capsules (170 mg/capsule) are prepared from the following ingredients.

| Dehydroevodiamine | 10 mg |
| --- | --- |
| Soybean oil | 160 mg |

Dehydroevodiamine (10 mg) is mixed with 160 mg of soybean oil. The resulting mixture is packed in soft capsules according to a conventional method using a rotary dies automatic molding machine.

EXAMPLE 11

A feed for a mouse (ration for one month) is prepared from the following ingredients.

| Hydroxyevodiamine | 0.03 g |
| --- | --- |
| Casein | 20 g |
| Lard | 10 g |
| Sucrose | 10 g |
| Mineral mixture | 4 g |
| Vitamin mixture | 1 g |
| Cellulose powder | 2 g |
| Sodium cholate | 0.125 g |
| Choline chloride | 0.2 g |
| Corn starch | 52.645 g |

EXAMPLE 12

Tea (1000 ml) is prepared from the following ingredients.

| Extract of *Evodia rutaecarpa* (Reference Example 1) | 5 g |
| --- | --- |
| Tea leaves | 15 g |

EXAMPLE 13

Tablets (300 mg/tablet) are prepared from the following ingredients according to a conventional method.

| Extract of *Evodia rutaecarpa* (Reference Example 1) | 50 mg |
| --- | --- |
| Lactose | 190 mg |
| Corn starch | 30 mg |
| Synthetic aluminum silicate | 12 mg |
| Carboxymethyl cellulose calcium | 15 mg |
| Magnesium stearate | 3 mg |

EXAMPLE 14

Chewing gum (30 pieces) is prepared from the following ingredients.

| Extract of *Evodia rutaecarpa* (Reference Example 1) | 1 g |
| --- | --- |
| Gum base | 25 g |
| Sugar | 63 g |
| Starch syrup | 10 g |
| Flavor | 1 g |

EXAMPLE 15

Candies (20 pieces) are prepared from the following ingredients.

| | |
|---|---|
| Extract of *Evodia rutaecarpa* (Reference Example 1) | 1 g |
| Sugar | 80 g |
| Starch syrup | 20 g |
| Flavor | 0.1 g |

EXAMPLE 16

Soft capsules (170 mg/capsule) are prepared from the following ingredients.

| | |
|---|---|
| Extract of *Fagara rhetza* (Reference Example 2) | 50 mg |
| Soybean oil | 120 mg |

The extract of *Fagara rhetza* (50 mg) is mixed with 120 mg of soybean oil. The resulting mixture is packed in soft capsules according to a conventional method using a rotary dies automatic molding machine.

EXAMPLE 17

Marmalade is prepared from the following ingredients.

| | |
|---|---|
| Extract of *Zanthoxylum rhetsa* (Reference Example 3) | 7 g |
| Feel of Chinese citrons | 500 g |
| Sugar | 200 g |

Juice obtained from one Chinese citron

EXAMPLE 18

A feed for sea breams is prepared from the following ingredients.

| | |
|---|---|
| Extract of *Araliopsis tabouensis* (Reference Example 4) | 10 g |
| Fish meal | 25 g |
| Chicken meal | 100 g |
| Meat and bone meal | 150 g |
| Fish soluble | 25 g |
| Soybean cake | 260 g |
| Wheat flour | 125 g |
| Corn | 250 g |
| Wheat germ | 40 g |
| Lucerne meal | 40 g |
| Salt | 5 g |
| Antioxidant | 20 g |

REFERENCE EXAMPLE 1

Process for Producing Extract of *Evodia rutaecarpa*

To 2.5 kg of fruits of *Evodia rutaecarpa* was added 10 l of ethanol, followed by maceration for 2 days. After collection of the extract, the same treatment was repeated twice to obtain 30 l of ethanol extract. The ethanol extract was filtered using a filter cloth (Miracloth, Hoechst Ltd.), and the filtrate was concentrated to dryness under reduced pressure to give 100 g of extract.

REFERENCE EXAMPLE 2

Process for Producing Extract of *Fagara rhetza*

To 200 g of bark of *Fagara rhetza* was added 1 l of ethanol, followed by maceration for 2 days. After collection of the extract, the same treatment was repeated twice to obtain 3 l of ethanol extract. The ethanol extract was filtered using a filter cloth (Miracloth, Hoechst Ltd.), and the filtrate was concentrated to dryness under reduced pressure to give 19.6 g of extract.

REFERENCE EXAMPLE 3

Process for Producing Extract of *Zanthoxylum rhetsa*

To 200 g of root bark of *Zanthoxylum rhetsa* was added 1 l of ehtanol, followed by maceration for 2 days. After collection of the extract, the same treatment was repeated twice to obtain 3 l of ethanol extract. The ethanol extract was filtered using a filter cloth (Miracloth, Hoechst Ltd.), an the filtrate was concentrated to dryness under reduced pressure to give 7.1 g of extract.

REFERENCE EXAMPLE 4

Process for Producing Extract of *Araliopsis tabouensis*

To 250 g of bark of *Araliopsis tabouensis* was added 1 l of chloroform, followed by maceration for 2 days. After collection of the extract, the same treatment was repeated twice to obtain 3 l of chloroform extract. The chloroform extract was filtered using a filter cloth (Miracloth, Hoechst Ltd.), and the filtrate was concentrated to dryness under reduced pressure to give 9.6 g of extract.

REFERENCE EXAMPLE 5

Determination of Evodiamine

The extracts obtained in Reference Examples 1–4 were respectively dissolved in ethanol to a concentration of 0.01% (w/v). Then, 10 μl of each solution was subjected to high performance liquid chromatography (Shimadzu Corporation, ODS column: 4.6 mm I.D. 25 cm, mobile phase: a 50% aqueous solution of acetonitrile, detection wavelength: 254 nm) to determine the evodiamine content.

The results are shown in Table 5.

TABLE 5

| Plants | Evodiamine content of dried extract %(w/w) |
|---|---|
| *Evodia rutaecarpa* (Reference Example 1) | 1.13 |
| *Fagara rhetza* (Reference Example 2) | 2.94 |
| *Zanthoxylum rhetsa* (Reference Example 3) | 0.014 |
| *Araliopsis tabouensis* (Reference Example 4) | 0.018 |

Industrial Applicability

The present invention provides a food, a drug and a feed which have lipid metabolism improving activity or anti-obesity activity.

We claim:

1. A food having lipid metabolism improving activity or anti-obesity activity which comprises, as an active ingredient, a compound selected from the group consisting of compounds represented by formula (I):

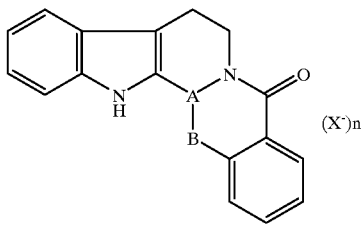

(I)

wherein >A—B— represents >CR$^1$—NR$^2$— (wherein R$^1$ represents hydrogen or hydroxy, and R$^2$ represents hydrogen or lower alkyl; or R$^1$ and R$^2$ are combined together to form a bond) or >C=N$^+$(R$^3$)— (wherein R$^3$ represents lower alkyl); n represents 0 when >A—B— is >CR$^1$—NR$^2$—, and represents 1 when >A—B— is >C=N$^+$(R$^3$)—; and X$^-$ represents an anion, and salts thereof (hereinafter collectively referred to as evodiamine compounds).

2. The food according to claim 1, which is obtained by adding an evodiamine compound to food materials containing substantially no evodiamine compound.

3. The food according to claim 1, which is obtained by adding a part of a plant containing an evodiamine compound, or a ground matter, extract, a partially-purified product or a purified product containing an evodiamine compound which is obtained from said part of the plant to food materials containing substantially no evodiamine compound.

4. The food according to claim 3, wherein said plant containing an evodiamine compound belongs to the family Rutaceae.

5. The food according to claim 3, wherein said plant containing an evodiamine compound belongs to a genus selected from the group consisting of Evodia, Fagara, Zanthoxylum and Araliopsis.

6. A feed having lipid metabolism improving activity or anti-obesity activity which comprises an evodiamine compound as an active ingredient.

7. The feed according to claim 6, which is obtained by adding an evodiamine compound to feed materials containing substantially no evodiamine compound.

8. The feed according to claim 6, which is obtained by adding a part of a plant containing an evodiamine compound, or a ground matter, extract, a partially-purified product or a purified product containing an evodiamine compound which is obtained from said part of the plant to feed materials containing substantially no evodiamine compound.

9. The feed according to claim 8, wherein said plant containing an evodiamine compound belongs to the family Rutaceae.

10. The feed according to claim 8, wherein said plant containing an evodiamine compound belongs to a genus selected from the group consisting of Evodia, Fagara, Zanthoxylum and Araliopsis.

11. A feed additive having lipid metabolism improving activity or anti-obesity activity which comprises an evodiamine compound as an active ingredient.

* * * * *

UNITED STATES PATENT AND TRADEMARK OFFICE
CERTIFICATE OF CORRECTION

PATENT NO. : 5,998,421

DATED : December 7, 1999

INVENTOR(S) :

YOSHIHARU YOKOO ET AL.

It is certified that error appears in the above-identified patent and that said Letters Patent is hereby corrected as shown below:

COLUMN 4

Line 8, "(*Aralioisis*" should read --(*Araliopsis*--.

COLUMN 5

Line 16, "*rutaecara*," should read --*rutaecarpa*,--;
Line 51, "35" should be deleted.

COLUMN 9

Table 3, "*rutaecaroa*," should read --*rutaecarpa*,--.

COLUMN 12

Example 12, after tea leaves 15 g, insert
 --Hot water (1000 ml) is poured for infusion.--

UNITED STATES PATENT AND TRADEMARK OFFICE
CERTIFICATE OF CORRECTION

PATENT NO.   : 5,998,421

DATED        : December 7, 1999

INVENTOR(S)  :

YOSHIHARU YOKOO ET AL.

It is certified that error appears in the above-identified patent and that said Letters Patent is hereby corrected as shown below:

<u>COLUMN 13</u>

Example 17, "Feel" should read --Peel--.

Signed and Sealed this

Twenty-fourth Day of April, 2001

Attest:

NICHOLAS P. GODICI

Attesting Officer     Acting Director of the United States Patent and Trademark Office